United States Patent
Roland et al.

(10) Patent No.: US 9,404,985 B2
(45) Date of Patent: Aug. 2, 2016

(54) METHOD AND MAGNETIC RESONANCE APPARATUS TO DETERMINE AT LEAST ONE DATUM FROM AN IMPLANTED SILICONE IMPLANT

(71) Applicants: Joerg Roland, Hemhofen (DE); Christian Schuster, Langenzenn (DE)

(72) Inventors: Joerg Roland, Hemhofen (DE); Christian Schuster, Langenzenn (DE)

(73) Assignee: Siemens Aktiengesellschaft, Munich (DE)

( * ) Notice: Subject to any disclaimer, the term of this patent is extended or adjusted under 35 U.S.C. 154(b) by 364 days.

(21) Appl. No.: 14/056,098

(22) Filed: Oct. 17, 2013

(65) Prior Publication Data
US 2014/0107470 A1    Apr. 17, 2014

(30) Foreign Application Priority Data
Oct. 17, 2012   (DE) .......................... 10 2012 218 913

(51) Int. Cl.
| A61B 5/055 | (2006.01) |
| G01R 33/46 | (2006.01) |
| A61B 5/00 | (2006.01) |
| G01R 33/485 | (2006.01) |

(52) U.S. Cl.
CPC ............ *G01R 33/4625* (2013.01); *A61B 5/004* (2013.01); *A61B 5/055* (2013.01); *A61B 5/4312* (2013.01); *A61B 5/4851* (2013.01); *G01R 33/485* (2013.01)

(58) Field of Classification Search
CPC ............ G01R 33/4625; G01R 33/485; A61B 5/4851; A61B 5/055; A61B 5/004; A61B 5/4312
See application file for complete search history.

(56) References Cited

U.S. PATENT DOCUMENTS

| 5,446,384 | A * | 8/1995 | Dumoulin .......... G01R 33/4828 324/307 |
| 7,084,626 | B2 | 8/2006 | Ma et al. |
| 7,358,729 | B2 | 4/2008 | Ma et al. |
| 2005/0030025 | A1* | 2/2005 | Ma .......................... A61B 5/055 324/309 |
| 2007/0253910 | A1* | 11/2007 | Ahrens .................. A61B 5/411 424/9.34 |
| 2011/0276135 | A1* | 11/2011 | Yacoub ..................... A61F 2/12 623/8 |

OTHER PUBLICATIONS

Birkefeld et al., "A study of the aging of silicone breast implants using 29Si, 1H relaxation and DSC measurements," Biomaterials, vol. 25 (2004), pp. 4405-4413.
Garrido et al., "Echo-Planar Chemical Shift Imaging of Silicone Gel Prostheses," Magnetic Resonance Imaging, vol. 11 (1993), pp. 625-634.

* cited by examiner

*Primary Examiner* — Jonathan Cwern
(74) *Attorney, Agent, or Firm* — Schiff Hardin LLP

(57) ABSTRACT

In a method and magnetic resonance apparatus to determine at least one datum of an implanted silicone implant, at least one magnetic resonance data set is acquired, with the acquired signals of the magnetic resonance data set originating at least in part from the silicone implant. At least one spectrum is calculated from the magnetic resonance data set, and the datum is determined in a processor from the spectrum.

9 Claims, 6 Drawing Sheets

METHOD AND MAGNETIC RESONANCE APPARATUS TO DETERMINE AT LEAST ONE DATUM FROM AN IMPLANTED SILICONE IMPLANT

BACKGROUND OF THE INVENTION

1. Field of the Invention

The present invention concerns a method to determine at least one datum of an implanted silicone implant.

2. Description of the Prior Art

Silicone implants are used in, among other things, the field of plastic surgery, and in particular for breast augmentation. Such implants have a casing (shell) of soft silicone (elastomer) and a filling. Common saline solution or different silicone gels are used as filling. Other filling materials have also already been tested, but common saline solution and silicone gels show the best chemical consistency.

After the implantation procedure, the silicone implant is no longer accessible. Situations can occur, however, in which it can be necessary, even years after the implantation, to obtain data about the implanted silicone implant.

For example, during manufacturing an impermissible substance may become included in a silicone implant, or it has turned out (sometimes after years-long studies) that contents of the silicone implants of specific manufacturers are to be considered a health concern or injurious. Industrial silicone may have been deliberately or accidentally used instead of medical silicone in the manufacture of a silicone implant.

In all of these cases it is desirable to be able to determine with certainty either the manufacturer or the product series or the condition of already-implanted silicone implants.

To find this information a patient may turn to the operating physician but in order for this physician to be able to answer the question, it is necessary that the product data of the silicone implant that is used be stored in association with the patient, and still be present even after years have passed, and the data must have been correct in the first place in order to be subsequently used in this context.

In the event that one of these requirements is not valid, an interventional or surgical procedure must be undertaken in which the silicone implant is exchanged, since a "biopsy" always damages the outer shell of the silicone implant, and therefore cannot be implemented.

SUMMARY OF THE INVENTION

An object of the present invention is to provide a method and apparatus with which at least one datum of an implanted silicone implant can be determined without an invasive procedure.

The above object is achieved in accordance with the present invention by a method to determine at least one datum of an implanted silicone implant, wherein a magnetic resonance data acquisition unit is operated in order to acquire at least one magnetic resonance data set that represents magnetic resonance signals originating at least in part from a silicone implant in an examination subject, and wherein the data set is provided to a processor and, in the processor, at least one spectrum is identified from the data set and the spectrum is used to determine at least one datum of the implanted silicone implant.

Magnetic resonance (MR) spectroscopy is an established spectroscopic method in which an examination subject is placed in a magnetic field, the protons or other nuclei that are capable of MR resonance in the examination subject are excited by an RF pulse or a series of RF pulses, and the energy that is received in such a manner is emitted again in the form of a detectable signal.

This signal is detected with a coil, and proceeds through multiple known processing steps into a memory, and is stored as raw data. A spectrum can be obtained from the raw data with additional known steps. The raw data must at least be Fourier-transformed. Naturally, other further processing steps (such as zero filling or a baseline correction) can also be taken.

Depending on the acquisition method, the spectrum of the detected signal can include water and fat peaks in addition to silicone peaks. These can either be suppressed or used as reference lines.

Since the filling of a silicone implant is a mixture of silicone gels and/or silicone oils and/or common saline solution, a somewhat different spectrum results for each manufacturer, as well as for each production line of a particular manufacturer. Each series run of silicone implants in which the composition of the contents of the shell and the filling is constant is designated herein as a production line.

The advantage of magnetic resonance spectroscopy is that the at least one datum can be obtained in vivo and non-invasively. As used herein, "datum" means an individual item of information, in particular pertaining to a feature of the silicone implant but not limited to a time (date) datum, for example.

The spectrum is preferably compared with at least one stored value and/or value range and/or spectrum, and the datum can be determined from such a comparison. The datum is thus determined using prior knowledge that can be present in different forms.

At least one datum can advantageously be associated with at least one value and/or value range and/or spectrum, or a group of values and/or value ranges. The acquired spectrum is a fingerprint (so to speak) of the silicone implant, and the respective fingerprints differ according to manufacturers and production lines. An automatic association is thus enabled by the comparison with known values.

If the spectra of the silicone implants of a manufacturer or of a product line of a manufacturer show a peak at a specific position (wavelength) in the spectrum, which peak is otherwise to be found in implants of no other manufacturer, or if a peak that is found in spectra of silicone implants of other manufacturers or other product lines is absent, an unambiguous association with a manufacturer or a product line can be made from the presence or the absence of a peak. Instead of the presence or absence of a single peak, the presence or absence of combinations of peaks, or the ratio of the signal intensities of specific resonances, can also be used as a conclusion criterion.

More or fewer unambiguous associations can take place depending on the divergence of the spectra of individual manufacturers and product lines. While the presence or absence of characteristic resonances allows an unambiguous limitation, even if such a limitation can only be made to multiple product lines or multiple manufacturers, this is no longer the case with the use of ratio values.

If a value of 1.5 is stored for the ratio of resonances A and B of a first manufacturer in the database and a value of 1.7 is stored for a second manufacturer, a value of 1.62 (which was determined from a spectrum measured at a patient) is not definitive as to one of the two manufacturers, but it might be thought that there is a certain tendency in the direction of the second manufacturer. Therefore, a probability can be associated with the values determined from a spectrum. This is a measure of how likely it is that the datum in question was correctly determined. From the interval of the database values and the measurement value, it can thus be established with 40% probability that the first manufacturer is the manufacturer of the measured silicone implant, and with 60% probability that the second manufacturer is the manufacturer of the measured silicone implant.

A manufacturer; or a group of manufacturers; or a manufacturing location; or a manufacturing time period; or a charge; or a material specification (in particular the silicone oils and gels that are used) can advantageously be stored as a datum. Every datum that can be relevant to identifying a particular silicone implant can be stored.

A chemical shift imaging acquisition method can advantageously be used in order to acquire the raw MR data. This is a method of spectroscopic imaging. In addition to the classical Chemical Shift Imaging (CSI), developments with improved sampling strategies of k-space also exist. For example, these include the Acquisition Weighted CSI (AW CSI) or Density Weighted CSI (DW CSI) acquisition methods. Furthermore, methods for what is known as fast spectroscopic imaging that function on the basis of SSFP additionally exist. The methods allow a two-dimensional and three-dimensional data acquisition.

Alternatively, a localized single volume spectroscopy acquisition method (also called single voxel spectroscopy) can be used to acquire the magnetic resonance data. In the acquisition of a non-localized spectrum, the entire volume of the examination subject that is located in the coil is excited and read out.

Generally, multiple RF coils (for example an excitation coil and a readout coil) can be used instead of a single RF coil. Coil arrays for parallel data acquisition can also be used.

Acquisition methods to acquire a localized spectroscopy data set are in particular PRESS or STEAM.

The diagnostic significance of the acquired spectra can be increased by the acquisition of signals from freely selectable volumes, for example by acquiring only signals from the casing or only from the filling. A spectrum calculated from the raw data then shows the resonances of a single substance or substance mixture, while the global acquisition of signals in each case is expanded by signals from the tissue of the examined patient that surrounds the silicone implant. The water resonance and the fat resonance can also be used as reference lines.

A reference substance can be used to scale the measured signals. This reference substance can have a liquid consistency or a consistency ranging from gelatinous to solid and, for example, can be packed into a cuvette and be placed into the measurement region, or the measurement region can be selected so that the cuvette is included. A numerical value is associated with the signal intensity of a predetermined resonance of the reference substance. A spectrum can be scaled to a reference value by means of the resonance of the reference substance, independent of apparatus settings and acquisition methods. This enables a significance to individual resonances of the spectrum to be imparted. Otherwise, it is only possible to draw conclusions about the ratios of the numerical values of different resonances (thus the relative signal intensity ratios) of a spectrum.

The values, value ranges or spectra can be stored in a database. This can be connectable with an update server via the Internet to update the database. However, the database can also be part of a learning system. A user can provide measurement of silicone implants with auxiliary information (such as the manufacturer or the manufacturing year) insofar as such information exists. This information can be used either to create new data sets or to verify or supplement already-present data sets.

The magnetic resonance data set can be acquired with a chest coil. Any coil that is desired for measurements in the chest region is thereby considered to be a chest coil. Such coils have already been developed for use in the field of breast cancer diagnosis, but can be used in the present context. The signal-to-noise ratio SNR can be improved with chest coils, so the reliability of the results increases with regard to ratios of resonances.

Instead of values or value ranges, a measured spectrum can be compared with stored spectra. For example, the autocorrelation value of two spectra can be determined. If the autocorrelation value of the measured spectrum and a stored spectrum exceeds a predetermined threshold, it is assumed that the measured spectrum is represented by the stored spectrum. The composition of the silicone implant measured in vivo accordingly coincides with that of the silicone implant upon which the stored spectrum is based. However, the composition of the latter silicone implant is known or can at the least be easily determined. Furthermore, additional product data (such as the production year, etc.) regarding the silicone implants can be known if such data are stored as well upon creation of the stored spectra.

In the simplest embodiment of the method according to the invention, the determined spectrum is examined for the presence of forbidden substances or contaminants. These can be identified using stored values and/or value ranges and/or spectra, for example if one or more peaks are present at resonance frequencies at which no peak is to be expected in the spectrum. The datum to be determined is then the impermissible resonance.

In a further embodiment, a material loss of the filling and/or the shell can be established by comparing at least one signal intensity or at least one relative signal intensity ratio with at least one stored value and/or value range and/or spectrum. This can occur if a material of the filling "evaporates", thus arrives into the surrounding tissue due to diffusion processes through the casing. Its signal intensity decreases in comparison to other signal intensities.

The invention also encompasses a magnetic resonance device that has a control device. The implementation of the aforementioned method in the control device can be implemented by the control device operating according to software, or the control device can be hard-wired (as hardware) for implementing the method.

The invention also encompasses a non-transitory, computer-readable data storage medium encoded with programming instructions that, when the storage medium is loaded into a computerized control and evaluation system of a magnetic resonance apparatus, cause the control and evaluation system to operate the magnetic resonance apparatus in accordance with one or more of the above-described embodiments of the method according to the invention.

DESCRIPTION OF THE PREFERRED EMBODIMENTS

Figure 1:
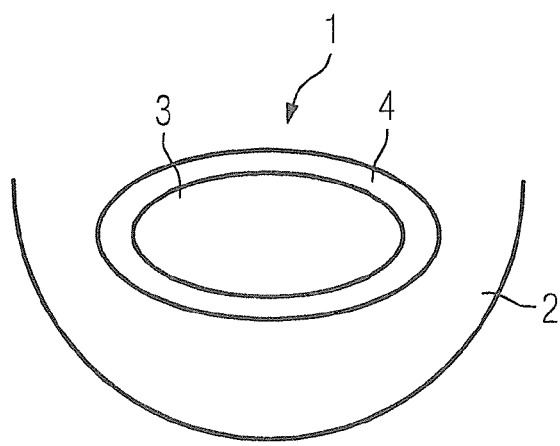
FIG. 1 shows an implanted silicone implant.

FIG. 1 shows in cross-section an implanted silicone implant 1 that was used within the scope of a breast enlargement in a breast 2. The silicone implant comprises a filling 3 and a shell 4 surrounding the filling 3.

Figure 2:
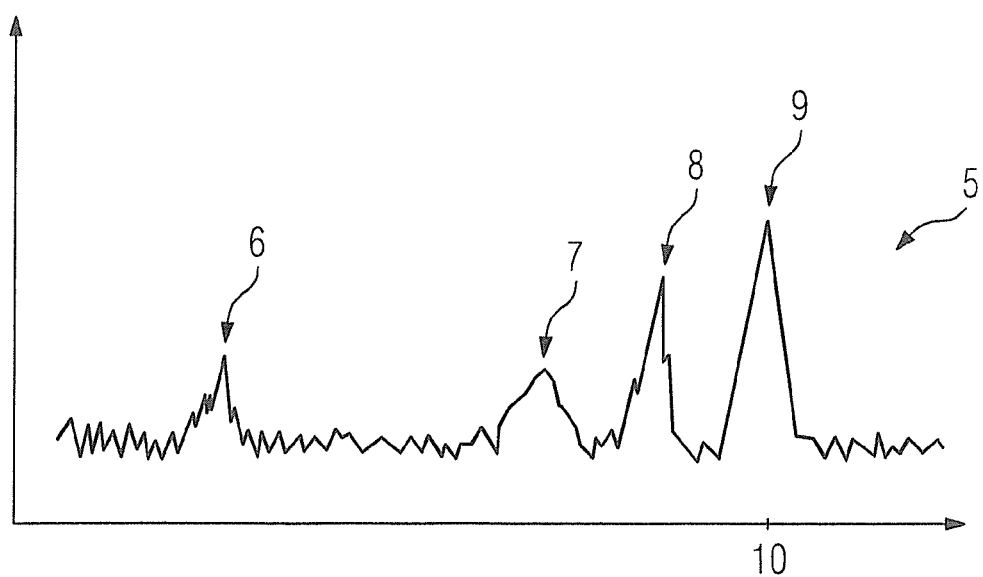
FIG. 2 shows a first example of a proton spectrum.

FIG. 2 schematically shows a proton spectrum 5 that was acquired with a non-localized method. The signals originate from the filling 3, the shell 4 and the breast 2, which is why the spectrum has a water peak 6, a fat peak 7 and a silicone peak 8. Furthermore, the spectrum includes a reference peak 9 that is caused by tetramethylsilane (TMS). TMS is a standard reference substance that is typically used to establish the zero point 10.

In order to be able to use the reference peak to scale the spectrum, multiple points are to be considered. For measurement—more precisely during the radiation of the RF pulses—a slice-selection gradient must be used, whereby a predetermined slice thickness is set. Furthermore, the TMS must be stored in a container with an established diameter, and completely fill the measurement slice. The acquisition method is to be standardized by the sequence, the echo time, the repetition time etc. being permanently preset. Additional variables may be set depending on the apparatus. These measures have the effect that the TMS has the same signal intensity at any apparatus. This can normally be set arbitrarily as long as only peaks of a single spectrum are compared. However, with the described steps a reference value (for example 1 or 100) can be associated with the reference spectrum 9. The signal intensities of the silicone peak 8 are can be compared not only with the water peak 6 and the fat peak 7 but also with silicone peaks from reference measurements. Since the water peak 6 and the fat peak 7 originate from signals from the breast tissue of the examination subject, their signal intensities are purely dependent on the person and of no importance with regard to the silicone implant.

The water peak 6 and the fat peak 7 can be suppressed with known RF pulse and magnetic field gradient combinations. These combinations are used as what are known as modules and, for example, are based on a frequency-selective saturation of the signal, which is why these resonances no longer have a peak in the spectrum.

The reference peak 9 can be used as described above in order to scale the spectrum 5. Conclusions about the implanted material and/or the manufacturer can then be drawn using the signal intensity of the silicone peak 8 relative to the reference peak 9 and/or the interval of peaks 8 and 9. For this, the relative signal intensity (dimensionless) and the peak interval (which is typically indicated in ppm) are compared with the values in a database.

Figure 3:
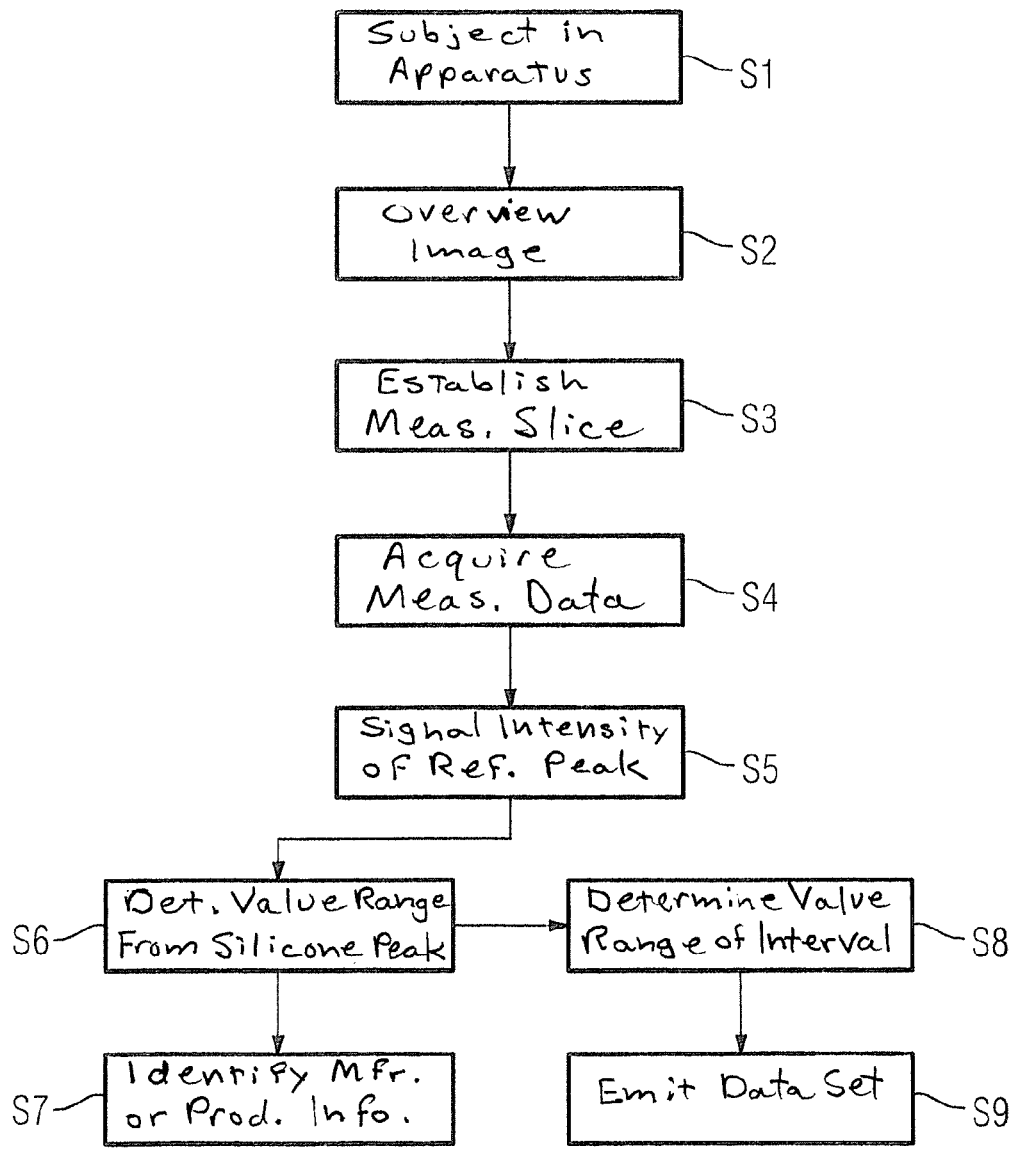
FIG. 3 is a flowchart of an embodiment of the method according to the invention.

FIG. 3 shows the steps to determine a manufacturer. After the examination subject is placed in a magnetic resonance apparatus in Step S1 and further standard procedures (such as what is known as shimming, the homogenization of the magnetic field in the measurement region) have been conducted, an overview image is acquired as Step S2. This is used in order to establish the measurement slice of the spectrum as Step S3. The field of view is placed so that a breast in cross section is included together with a reference tubule with reference substance. The measurement plane is therefore situated parallel to the longitudinal axis of the examination subject.

The coil used for acquisition is advantageously a breast coil that can in particular be adapted to different breast shapes. The SNR can be increased with such a coil, and at the same time the resolution can be improved.

In a next Step S4, the measurement data are acquired and stored at least in a volatile memory. Any arbitrary sequence can be used as a sequence, wherein slice-selection gradients are switched relative to the RF pulses so that only the signals from one slice are acquired. Furthermore, the raw data are subjected to post-processing steps in order to generate a spectrum.

In order to scale the spectrum, the signal intensity of the reference peak 9 is determined as Step S5. The maximum value of the resonance is thereby designated with the signal intensity of a peak. From this value, a scaling factor is calculated in order to set the signal intensity of the reference peak 9 to a predetermined value (for example a value of 100). At least the signal intensity of the silicone peak 8 is multiplied by this scaling factor. Furthermore, the interval of peaks 8 and 9 is determined.

In Step S6, a value range with which the values stored in a database are compared is determined from the scaled signal intensity of the silicone peak 8. If a value lies within the value range, it is stored for further review; otherwise, the data set is discarded. If all data sets are reviewed, a check is made as to how many values or, respectively, data sets have been stored. In the event that only one data set has been stored, the review is ended. As Step S7, the manufacturer or, respectively, the production line or the production year that is stored in the data set is then output.

Otherwise, in Step S8 a value range is likewise determined from the interval of the peaks 8 and 9 and compared with the remaining data sets. All data sets that do not satisfy this criterion are likewise discarded. The remaining data set or data sets are output in Step S9. In the event that more than one data set remains, these can be provided with probability information as described above.

In spite of multiple remaining data sets, after Step S6 the method can conclude with Step S7 if all remaining data sets satisfy a type of non-criticality criterion. Solely as an example, if only the implants of a specific manufacturer are sought (since this has processed forbidden ingredients in one or more production lines), a non-criticality criterion is such that the manufacturer of the silicone implant that has been measured is not the sought manufacturer.

Figure 4:
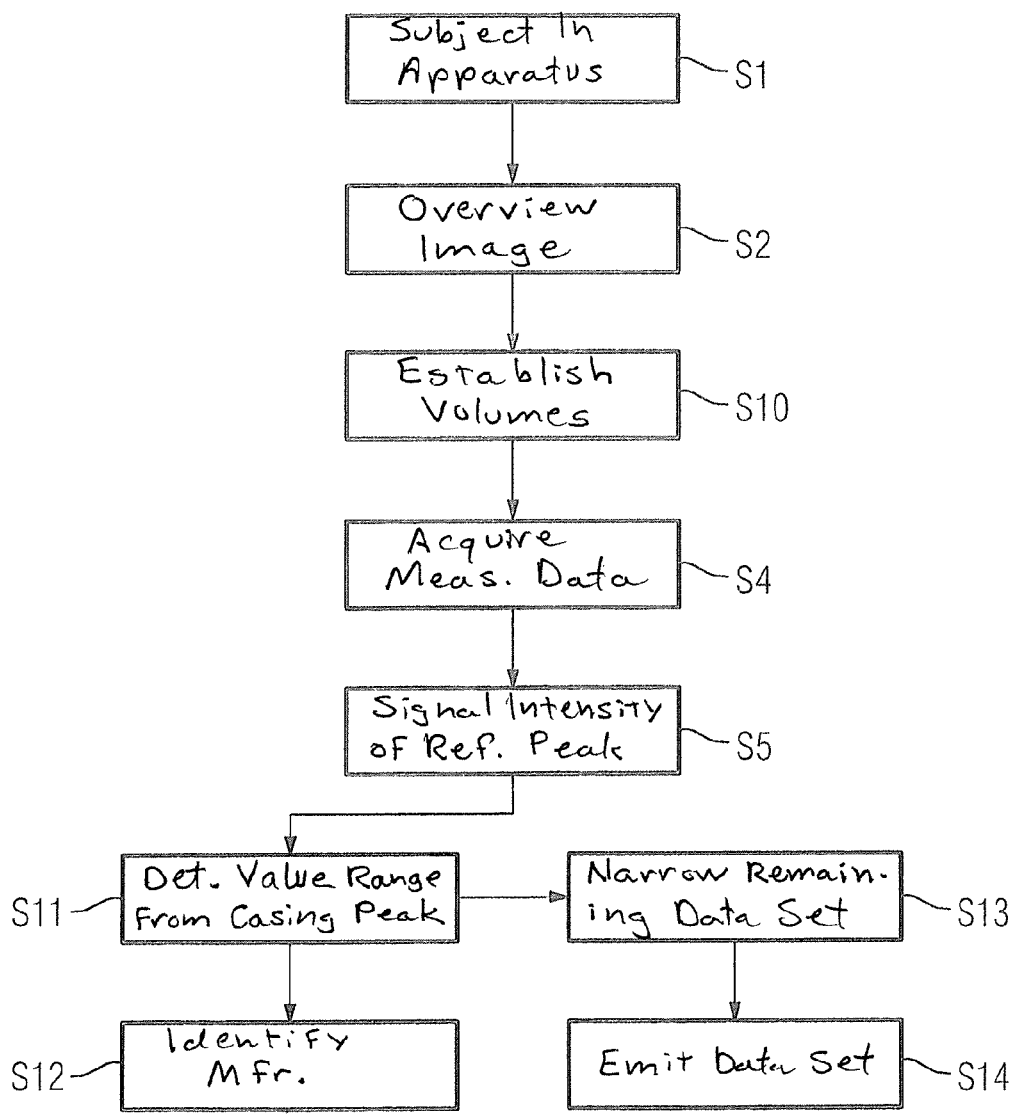
FIG. 4 is a flowchart of a further embodiment of the method according to the invention.

Alternatively (as FIG. 4 shows), instead of Step S3 (and the slice selection taking place there) volumes inside the filling 3, the casing 4 and the reference substance can be established as Step S10. The 3 spectra acquired in such a manner respectively show at least one peak. The peak in the spectrum of the reference substance is in turn used for scaling in the two other spectra as well. This is possible if the acquisition parameters remain consistent with the exception of the gradients that are switched for localization.

Instead of Steps S6 through S9, Steps S11 through S14 are executed, wherein instead of the silicone peak 8 the silicone peak 11 (that was acquired from the signal from the casing 4) is used to determine a value range (Step 11), which in Step S12 leads (analogous to Step S7) to the output of the manufacturer. The signal intensity of the silicone peak 12 of the filling 3 or of the value range calculated from this is used as a Step S13 to further narrow the remaining data sets. The output takes place in Step S14.

Figure 5:
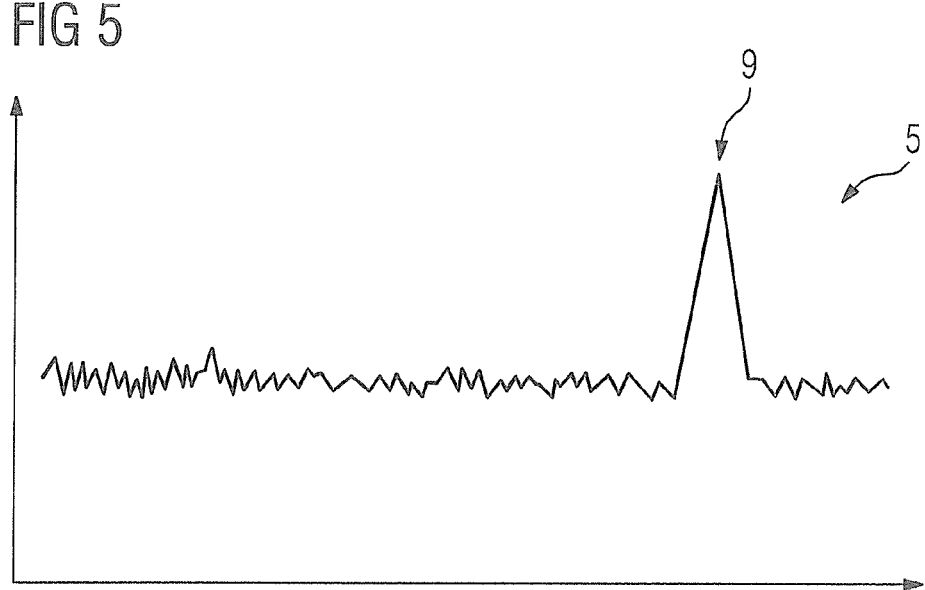
FIG. 5 shows a second example of a proton spectrum.
Figure 6:
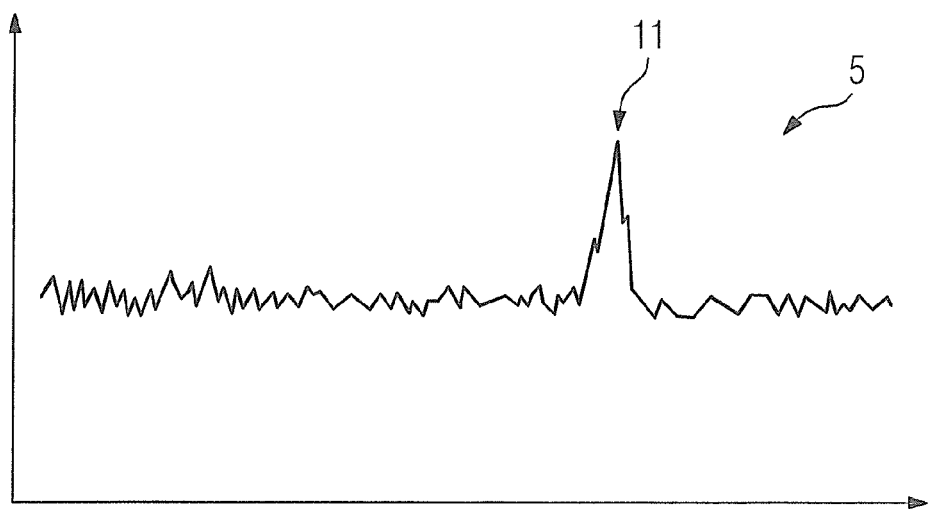
FIG. 6 shows a third example of a proton spectrum.
Figure 7:
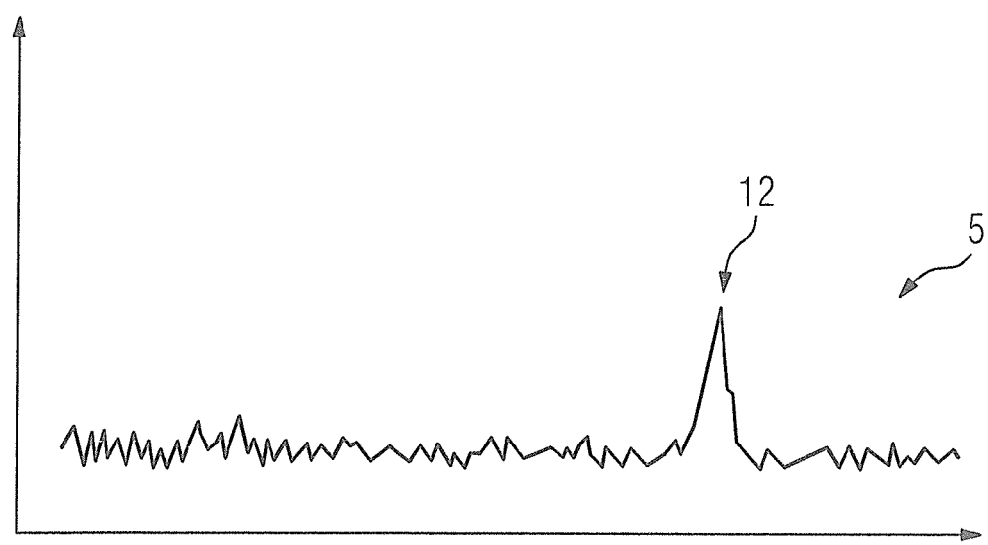
FIG. 7 shows a fourth example of a proton spectrum.

The spectra that are measured in an examination according to FIG. 4 are shown in FIGS. 5 through 7. FIG. 5 shows a spectrum with a reference peak 9; FIG. 6 shows a spectrum with a silicone peak 11 that was generated from signals from the shell 4; and FIG. 7 shows a spectrum with a silicone peak 12 that was acquired from signals from the filling 3.

In principle, the procedure described with regard to FIGS. 3 and 4 is thus identical except for the type of data acquisition and the evaluation adapted to this. In the embodiment according to FIG. 4, the interval of peaks cannot be used as long as a reference resonance is not present in all spectra.

In an alternative, instead of value comparisons the autocorrelation value with stored spectra can be determined. If this exceeds a threshold, an association with manufacturers or product lines takes place.

Figure 8:
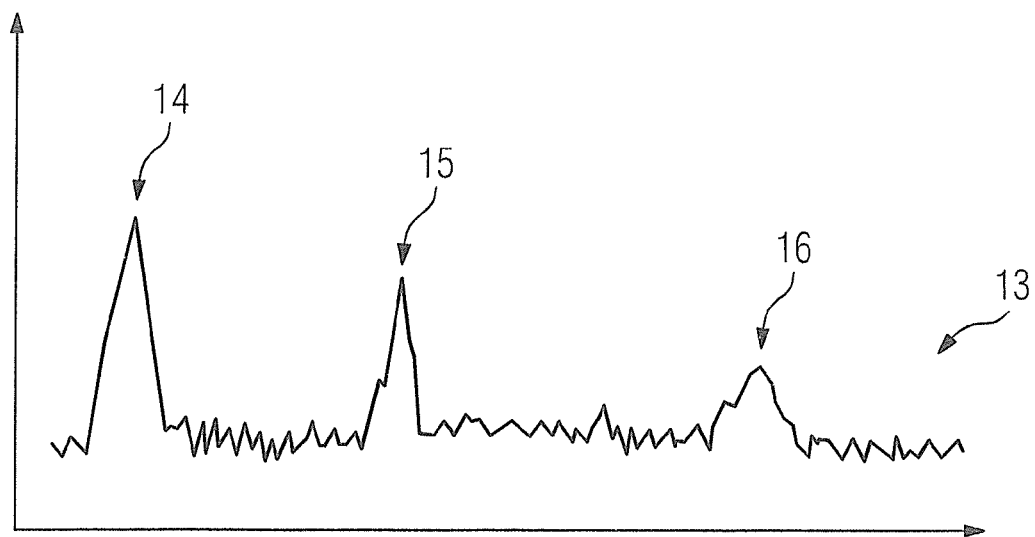
FIG. 8 shows a silicon spectrum.

Instead of the acquisition of proton spectra (also designated as 1H spectra), it is also possible to acquire 29Si spectra (thus silicon spectra). Such a spectrum 13 is shown in FIG. 8. Since the silicone has different monomers, it has a number of resonances. Their signal intensities depend on the respective distribution of the monomers; the presence of specific peaks (purely as an example the silicone peak 14) or the ratio of the signal intensities of two peaks (for example the signal intensity of the silicone peak 15 relative to the signal intensity of the silicone peak 16) is therefore characteristic of the origin of the silicone implant. Manufacturer and product lines can be identified or excluded analogous to the procedure describe with regard to the proton spectra. Due to the multiple resonance lines in the silicon spectrum, more decision criteria are provided, which increases the reliability of the results.

Since silicon has a lower nucleus-specific sensitivity than hydrogen, and therefore requires a longer measurement time, an interleaved measurement design with a double-resonant coil (in particular a double-resonant breast coil) is preferably used for measurement. A double-resonant coil is a coil that can simultaneously transmit and/or receive at two resonance frequencies, for example the proton resonance frequency and the silicon resonance frequency. This enables a simultaneous measurement of the proton and silicon spectra, whereby the total measurement time is reduced.

Proton spectra can also have more than one silicone peak 8. This depends on the composition of the silicone gels and oils of the casing 4 and the filling 3.

Figure 9:
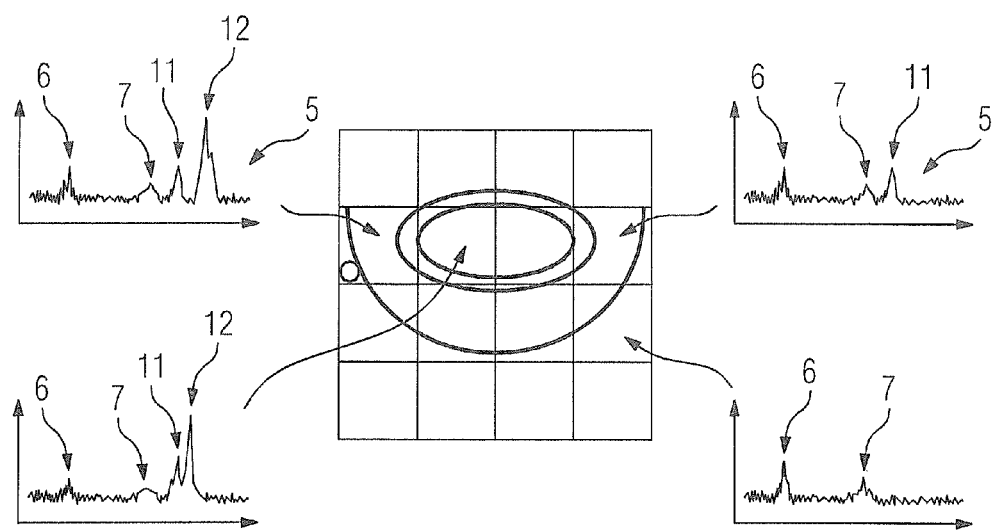
FIG. 9 shows a spectroscopic image.

FIG. 9 shows an image that was acquired by spectroscopic imaging. Each image element is determined from an associated spectrum. It is thus possible to show a separate image with regard to every resonance or every arbitrary frequency range. An association of the spectra with, for example, the shell 4 or the filling 3 likewise takes place due to the spatial association of the spectra with image regions.

The spectroscopic image according to FIG. 9 has a resolution of 4×4 image elements, and therefore does not show the breast 2 and the silicone implant 1 as presented but rather only shows a greyscale value per image element. The breast 2 and the silicone implant 1 were highlighted in order to clarify the composition of the spectra. For example, only with regard to the image element including the reference substance shows a reference peak 9. The silicone peaks 11 and 12 of the shell 4 and the filling 3 can only be located in the spectrum for which signals originate from the shell 4 and the filling 3. Local conspicuities in a silicone implant 1 can also be detected.

The evaluation of spectra (in particular the spectra of a spectroscopic image) automatically takes place with software. Algorithms to fit (match) spectra are known and have been used for a long time.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method to determine at least one manufacturing attribute of an implanted silicone implant, comprising:
   operating a magnetic resonance data acquisition unit to acquire at least one magnetic resonance data set representing magnetic resonance signals originating at least in part from a silicone implant in an examination subject;
   providing said at least one magnetic resonance data set to a processor and, in said processor, calculating at least one calculated spectrum from said at least one magnetic resonance data set and comparing said calculated spectrum to at least one stored item selected from the group consisting of a stored spectrum value, a stored spectrum value range, and at least one set of stored data representing a spectrum in order to associate at least one manufacturing attribute with the implanted silicone implant, said at least one manufacturing attribute being selected from the group consisting of a manufacturer of the implanted silicone implant, a group of manufacturers of the implanted silicone implant, a manufacturing site for the silicone implant, a manufacturing time period of the silicone implant, and a composition of gels and oils present in the silicone implant; and
   making a designation of said manufacturing attribute available from said processor as an output in electronic form.

2. A method as claimed in claim 1 comprising associating said at least one manufacturing attribute by associating a comparison result, obtained by said comparing of said spectrum with said at least one stored item, with a further item selected from the group consisting of at least one value, at least one set of data representing a value range, at least one spectrum, a group of values, and a group of value ranges.

3. A method as claimed in claim 1 comprising operating said magnetic resonance data acquisition unit according to a chemical shift imaging acquisition method to acquire said at least one magnetic resonance data set.

4. A method as claimed in claim 1 comprising operating said magnetic resonance data acquisition unit with a localized spectroscopy acquisition method to acquire said at least one magnetic resonance data set.

5. A method as claimed in claim 4 comprising acquiring said magnetic resonance signals from a shell of the silicone implant, and using the magnetic resonance signals acquired from the shell of the silicone implant to calculate said spectrum.

6. A method as claimed in claim 4 comprising acquiring said magnetic resonance signals from filling in the silicone implant, and using the magnetic resonance signals acquired from the filling of the silicone implant to calculate said spectrum.

7. A method as claimed in claim 1 comprising operating said magnetic resonance data acquisition unit to acquire said at least one magnetic resonance data set from a breast of the examination subject, using a breast coil.

8. A magnetic resonance apparatus comprising:
   a magnetic resonance data acquisition unit;
   a control unit configured to operate the magnetic resonance data acquisition unit to acquire at least one magnetic resonance data set from an examination subject located in the data acquisition unit, said at least one magnetic resonance data set representing signals originating at least in part from a silicone implant implanted in the examination subject; and
   a computerized processor provided with said at least one magnetic resonance data set, said processor being configured to calculate at least one calculated spectrum from the at least one magnetic resonance data set and to compare the calculated spectrum to at least one stored item selected from the group consisting of a stored spectrum value, a stored spectrum value range, and at least one set of stored data representing a spectrum in order to associate at least one manufacturing attribute with the implanted silicone implant, said manufacturing attribute being selected from the group consisting of a manufacturer of the implanted silicone implant, a group of manufacturers of the implanted silicone implant, a manufacturing site for the silicone implant, a manufacturing time period of the silicone implant, a composition of gels and oils present in the silicone implant, and to make a designation of said manufacturing attribute available at an output of the processor in electronic form.

9. A non-transitory, computer-readable data storage medium encoded with programming instructions, said data storage medium being loaded into a computerized control and evaluation system of a magnetic resonance apparatus, that also comprises a magnetic resonance data acquisition unit, said programming instructions causing said control and evaluation system to:

operate the data acquisition unit to acquire at least one magnetic resonance data set from an examination subject located in the data acquisition unit, said at least one magnetic resonance data set representing magnetic resonance signals originating at least in part from a silicone implant implanted in the examination subject;

calculate at least one calculated spectrum from the at least one magnetic resonance data set; and compare the calculated spectrum to at least one stored item selected from the group consisting of a stored spectrum value, a stored spectrum value range, and at least one set of stored data representing a spectrum in order to associate at least one manufacturing attribute with the implanted silicone implant, said manufacturing attribute being selected from the group consisting of a manufacturer of the implanted silicone implant, a group of manufacturers of the implanted silicone implant, a manufacturing site for the silicone implant, a manufacturing time period of the silicone implant, a composition of gels and oils present in the silicone implant, and make a designation of the manufacturing attribute available in electronic form at an output of the control and evaluation system.

* * * * *